United States Patent [19]
Ootani et al.

[11] Patent Number: 5,501,838
[45] Date of Patent: Mar. 26, 1996

[54] AUTOMATED IMMUNOCHEMICAL ANALYZER

[75] Inventors: Toshihiro Ootani; Takayoshi Izumi, both of Kobe, Japan

[73] Assignee: Toa Medical Electronics Co., Ltd., Kobe, Japan

[21] Appl. No.: 367,824

[22] Filed: Jan. 3, 1995

Related U.S. Application Data

[63] Continuation of Ser. No. 35,620, Mar. 23, 1993, abandoned.

[30] Foreign Application Priority Data

Apr. 3, 1992 [JP] Japan ................................ 4-112150

[51] Int. Cl.$^6$ ..................................................... G01N 35/02
[52] U.S. Cl. ................................ 422/65; 422/63; 422/67; 422/105; 422/117; 436/43; 436/47; 436/49; 436/50; 436/55; 436/174; 436/180
[58] Field of Search ................................ 422/63, 65, 67, 422/99, 100, 102, 104, 105, 117, 119; 436/43, 47, 48, 50, 55, 180, 809, 49, 174

[56] References Cited

U.S. PATENT DOCUMENTS

| | | | |
|---|---|---|---|
| 4,582,990 | 4/1986 | Stevens | 250/328 |
| 4,931,256 | 6/1990 | Mack et al. | 422/65 |
| 4,952,518 | 8/1990 | Johnson et al. | 436/518 |
| 5,008,082 | 4/1991 | Shaw | 422/65 |
| 5,055,263 | 10/1991 | Meltzer | 422/65 |
| 5,055,408 | 10/1991 | Higo et al. | 436/48 |
| 5,104,621 | 4/1992 | Pfost et al. | 422/67 |
| 5,158,895 | 10/1992 | Ashihara et al. | 436/526 |

*Primary Examiner*—Jill Warden
*Assistant Examiner*—Long V. Le
*Attorney, Agent, or Firm*—Jones, Tullar & Cooper

[57] ABSTRACT

A small, inexpensive, and easy-to-use automated immunochemical anlayzer is provided. The automated immunochemical analyzer comprises at least one reaction plate of disposable type forming a plurality of containers in one body, a table that can be drawn out for mounting the reaction plates, a table can be drawn out for mounting specimen racks, a reagent thermostatic unit, a reaction thermostatic unit, a reaction plate holding part, an apparatus for aspirating and discharging sample liquid, and an XY moving part mounting the reaction plate holding part and the apparatus for aspirating and discharging sample liquid. First, by the XY moving part, the holding part holds the reaction plate before use from the table for mounting the reaction plates and moves up to the reaction thermostats unit. Consequently, by the XY moving part, the apparatus for aspirating and discharging sample liquid is moved reciprocally among the specimen rack, reagent thermostatic unit, and reaction thermostatic unit, thereby distributing specimens and reagents to the reaction plate. THe distributed liquid is kept in a thermostatic state, and shaken and agitated, thereby promoting the antigen-antibody reaction. The reaction liquid is sample by the apparatus for aspirating and discharging sample liquid, and is measured.

6 Claims, 9 Drawing Sheets

5,501,838

AUTOMATED IMMUNOCHEMICAL ANALYZER

This is a continuation of application Ser. No. 08/035,620 filed on Mar. 23, 1993, now abandoned.

BACKGROUND OF THE INVENTION

The present invention relates to an automated immunochemical analyzer capable of quantitating antigens or antibodies by individually counting the number of particles of aggregates (agglutinated matter) of insoluble carriers produced by antigen-antibody reaction.

The CIA method is known as a procedure for measuring trace tumor related protein, such as alpha-fetoprotein (AFP) and carcinoembryonic antigen (CEA), promptly and at high sensitivity. CIA or counting inmmunoassay, is a method to quantitate the target antigen (or antibody) in the specimen by mixing the specimen containing the target antigen (or antibody), and a reagent containing latex particles bonded with antibody (or antigen) specifically reacting with the antigen (or antibody) in the specimen, Forming latex aggregates by antigen-antibody reaction, measuring the particles of the aggregates, calculating the degree of aggregation from the unaggregated particle count and aggregated particle count, and converting into the concentration of antigen (or antibody). An automated immunochemical analyzer by the CIA method has been disclosed, for example, in Published Unexamined Japanese Patent Application Hei. 1-259257.

In the conventional automated immunochemical analyzer, aspiration and discharge means are individually installed for the specimen, reagent and reaction liquid, and aspiration, discharge and cleaning (rinsing) are performed by rotating the arm furnished with a pipet, and moving the pipet in the arc direction.

For aspiration and discharge of a plurality of specimens, reagents and reaction liquids, it is necessary to move the object container during the circulation motion of the piper, which is realized by rotating the tables mounting the plurality of specimen containers, with at least one reagent container and at least one reaction container.

The reaction containers are cleaned in the apparatus by cleaning means after use.

Therefore, the apparatus is complicated, and a wide space for turntables is necessary. As a result, the apparatus becomes larger in size and higher in price.

During reaction or measurement, the turntables and aspiration and discharge means cooperate, and it has been difficult to add the specimens to be measured or to be squeezed by emergency specimens. Besides, depending on the measuring items, the contamination problem has been caused even after cleaning the reaction container.

OBJECT AND SUMMARY OF THE INVENTION

It is therefore a primary object of the present invention to provide an automated immunochemical analyzer which solves the above noted problems and is of high precision, small in size, low in price, and easy to use.

To achieve the above object, the present invention provides an automated immunochemical analyzer comprising:

at least one reaction plate 12 on which a plurality of reaction containers 14 are formed integrally, a table 10 for the reaction plates that can be drawn out on which the reaction plates are disposed before use and the after use, a table 34 for a specimen rack that can be drawn out and on which a plurality of specimen racks 36 are disposed, a reagent thermostatic unit 44 for keeping reagents in the thermostatic (constant temperature) state, a reaction thermostatic unit. 58 for shaking the reaction plate 12 while holding (keeping) the thermostatic (constant temperature) state, a reaction plate holding part 90 for holding and lifting the reaction plate 12, means 66 for aspirating and discharging sample liquid for aspirating and discharging a specific amount of specimen and reagent from a piper 82, and an XY moving part 70 containing the reaction plate holding part 90 and the means 66 for aspirating and discharging sample liquid.

The reaction plate 12 is of the disposable type, and is discarded (dumped) after use without being cleaned.

First, by the XY moving part 70, the holding part 90 is moved from the table 10 up to the reaction thermostatic unit 58 while holding the reaction plate before use. Consequently, by the XY moving part 70, the means 66 for aspirating and discharging sample liquid is moved reciprocally among the specimen rack 36, reagent thermostatic unit 44 and reaction thermostatic unit 58, and distributes specimen and reagent in the reaction plate. The distributed liquid is kept thermostatically (at constant temperature), shaken, and agitated, and the antigen-antibody reaction is promoted. The reaction liquid is sampled by the means 66 for aspirating and discharging sample liquid, and is measured.

DETAILED DESCRIPTION OF THE PREFERRED EMBODIMENTS

Figure 1:
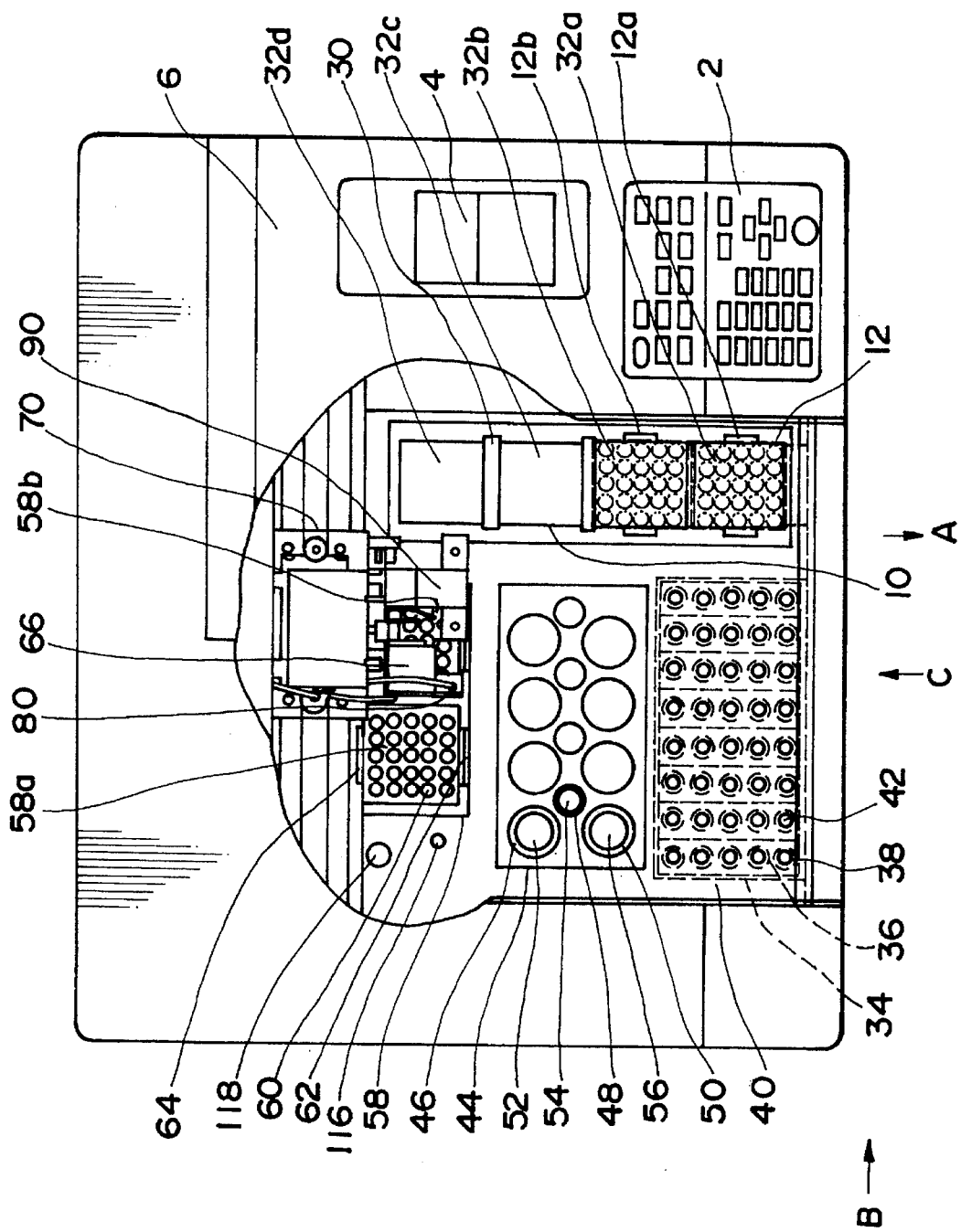
FIG. 1 is an explanatory plan view showing an embodiment of an automated immunochemical analyzer of the present invention.

Referring now to the drawings, some of the preferred embodiments of the present invention are described in detail below.

FIG. 1 is a plan view of an embodiment of an automated immunochemical analyzer of the present invention. The basic construction of the reaction system and measurement system is the same as the apparatus disclosed in the Published Unexamined Japanese Patent Application No. Hei. 1-259257. The apparatus of the present invention is downsized in order to reduce the cost of that conventional apparatus. A principal difference is the use of disposable reaction plates. As a result, the cleaning device is not needed. Besides, using only one means for aspirating and discharging liquid, the means is moved two-dimensionally, and the move of other units is eliminated, and the means is provided with a function for holding the reaction plate, so that an effective use of space and a saving of cost are realized.

By reference to FIG. 1, a general construction of the automated immunochemical analyzer of the present invention is described below.

Numeral 10 is a table for reaction plates 12 Numeral 34 is a table for specimen racks 3b Numeral 44 is a reagent thermostatic unit for keeping reagents in a thermostatic (constant temperature) state. Numeral 58 is a reaction thermostatic unit for maintaining the thermostatic state while shaking and agitating a reaction liquid (a mixed liquid of specimen and reagents). Numeral 66 is a means for aspirating and discharging sample liquid. Numeral 90 is a holding part for holding reaction plates 12. The means 66 for aspirating and discharging sample liquid and the holding part 90 are mounted on the same XY moving part 70, and are moved back and forth, right and left. Numeral 2 denotes an operation panel for setting and entering data. Numeral 4 is a printer, and 6 is a display unit.

The construction of each part is described in further detail below.

Figure 2:
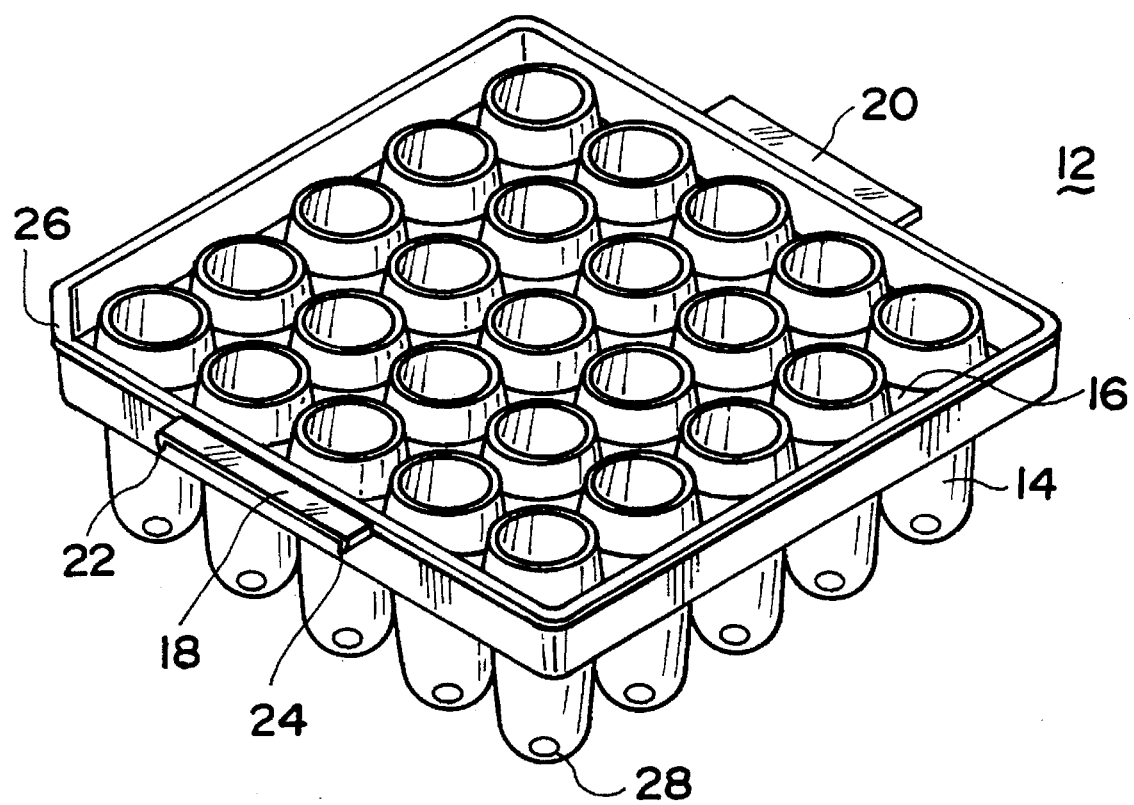
FIG. 2 is a perspective view showing an example of a reaction plate used in the apparatus of the present invention.

FIG. 2 is a perspective view of an example of a reaction plate 12 used in the apparatus of the present invention. The reaction plate 12 is made of synthetic resin. One plate holds, for example, a total of 25 reaction containers 14 in 5 rows and 5 columns, and these containers 14 are linked with each other by a base plate 16. All the containers 14 are formed in one body. The inside diameter and height of the containers 14 are, for example, about 8 mm and about 24 mm, respectively. As seen from the top, the reaction plate 12 has a square shape of one side of, for example, about 70 mm.

At both sides of the reaction plate 12, handles 18, 20 for holding the reaction plate are attached. At both sides of the handles 18, 20, moreover, since protrusions. 22, 24 for holding are provided downward, so that holding of the reaction plate is much easier, while the positional deviation of the reaction plate when moving is prevented.

Details are described below.

The upper end and outer frame of each container 14 are located higher than the position of the base plate 16 (for example, 6 mm), and the liquid in the containers hardly splashes out. The liquid spilling over the base plate 16 hardly gets into the containers 14. A corner 26 of the reaction plate 12 is partly cut for positioning purposes. In the bottom of each container 14, a recess 28 is formed. Stable dimensions are obtained in manufacture, and it is possible to install the reaction plate 12 in the apparatus securely. The reaction plate should be preferably made entirely of a transparent body.

Referring back to FIG. 1, the explanation continues.

The table 10 for mounting the reaction plates 12 is partitioned by, for example, three partition members 30, so that four reaction plates may be disposed. The locations at which the reaction plates 12 are disposed are supposed to be, from the nearest side (the lowest side in FIG. 1), with the first place being at 32a, the second place being at 32b, third place being at 32c, and the fourth place being at 32d. The first and second places 32a, 32b are the spaces for placing the reaction plates 12a, 12b before use. The third and fourth places 32c, 32d are spaces for placing the reaction plates after use, and the third and fourth places 32c, 32d are empty (open) before use. When the measurement ends, the reaction plates 12a, 12b are used as the measurement starts, they are put in the places 32c, 32d.

Figure 3:
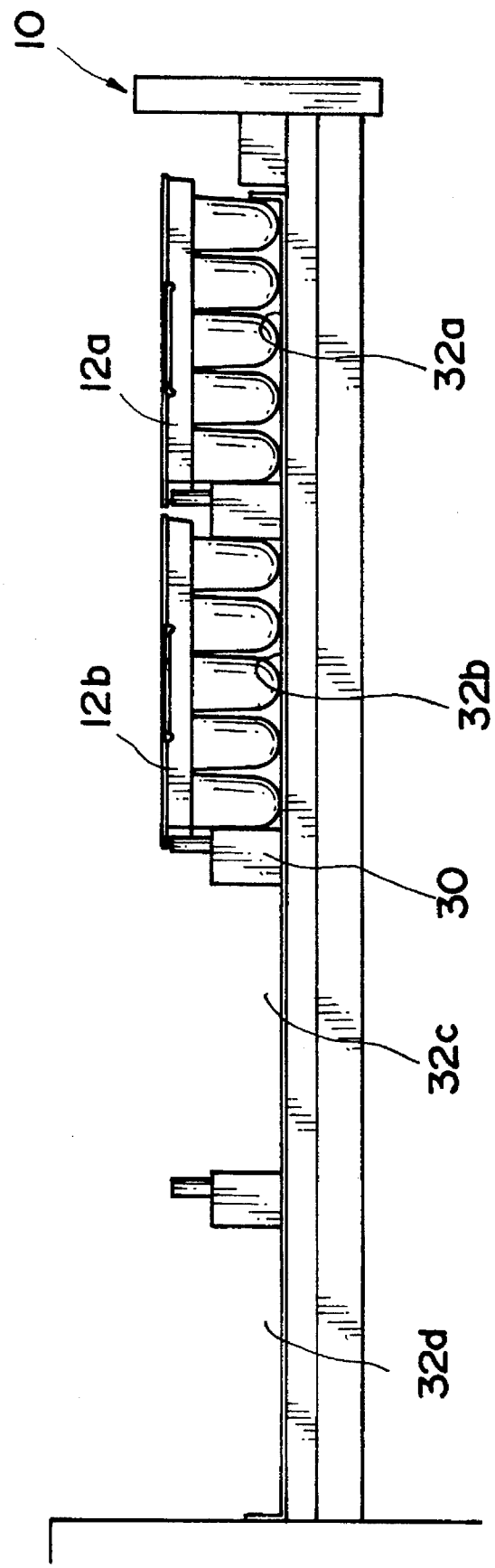
FIG. 3 is an explanatory diagram showing the drawn state of the table for a reaction plate as seen from the direction of arrow B in FIG. 1 (a side explanatory diagram around the table for the reaction plate).

The table 10 can be drawn out in the direction of arrow A in FIG. 1. FIG. 3 is a view in the direction of arrow B in FIG. 1, showing the state of the table 10 being drawn out. By drawing out the table 10, the reaction plate 12 can be inserted or taken out easily.

On the table 34, for example, up to eight specimen racks 36 can be mounted. One specimen rack can hold, for example, five specimen containers 38. The specimens are human serum, plasma or urine. Each specimen is aspirated and sampled through a penetration hole 42 of a chassis 40. The table 34 can be also drawn out in the direction of arrow A, the same as the table 10 for the reaction plate.

Figure 4:
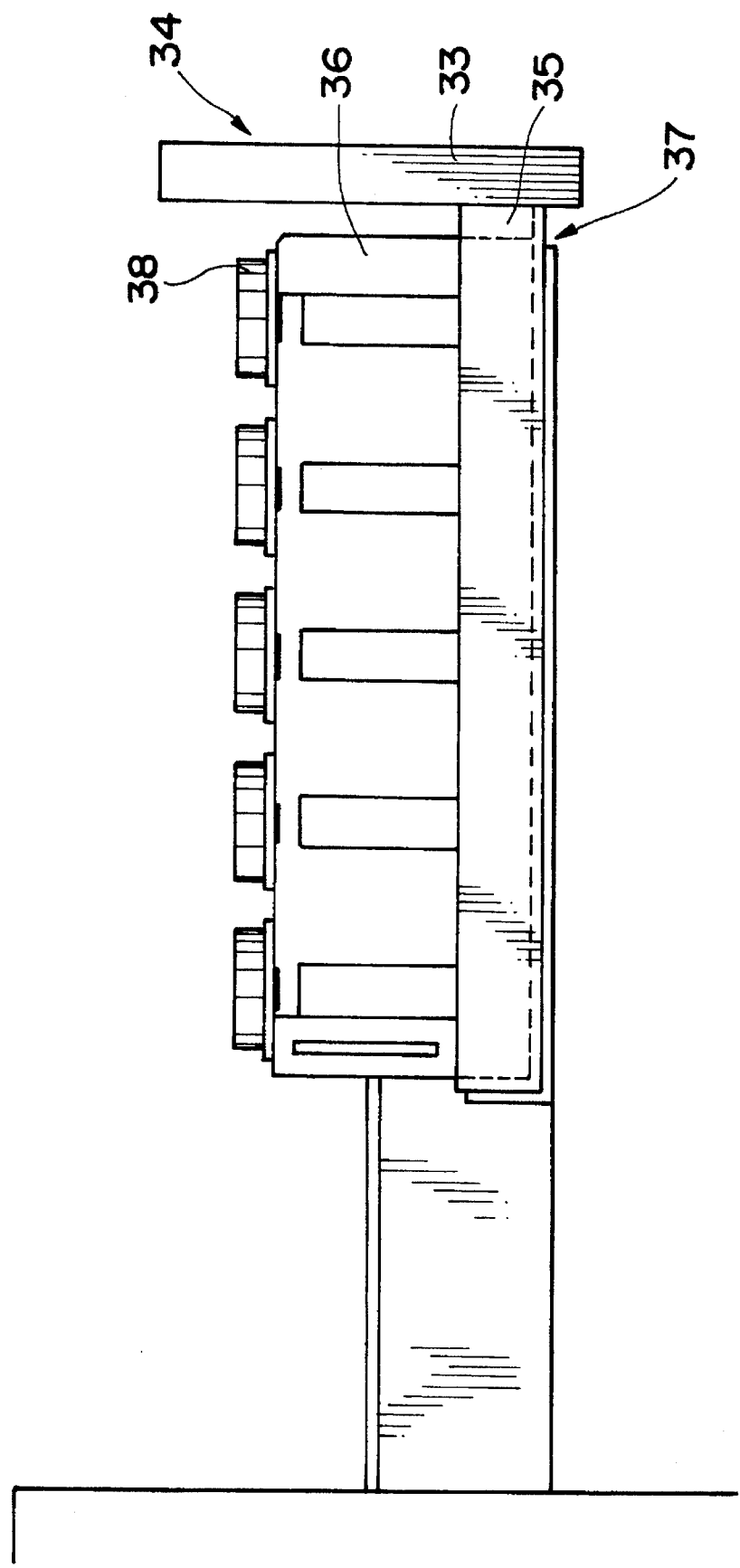
FIG. 4 is an explanatory diagram showing the drawn state of the table for a specimen rack as seen from the direction of arrow B in FIG. 1 (a side explanatory diagram around the table for the specimen rack).

FIG. 4 is a view in the direction of arrow B in FIG. 1, showing the state of the table 34 being drawn out. A mounting table 37 comprising a front panel 33 and a bottom plate 35 can be drawn out. The specimen rack is placed or taken out by drawing out or removing the table 34. Usually, places for six racks on the left side are used, and the places for two racks on the right side are kept open for emergency specimens.

On the back side of the reagent thermostatic unit 44, a cooler (not shown) is provided, and the reagents are kept at about 15° C. or less. On the top of the reagent thermostatic unit 44, recesses 46, 48, 50 are provided, and buffer solution container 52, latex reagent container 54, and diluent liquid container 56 are put in the recesses.

A reaction plate 12 is put on the reaction thermostatic unit 58, and the reaction liquid which is a mixed liquid of specimen and reagents is kept around 45° C. by a heater (not shown) attached to the back side of the reaction thermostatic unit 58. Furthermore, the entire reaction thermostatic unit 58 generates shaking motions. The radius of rotation of the shaking motions is, for example, 1.5 mm, and the rotating speed is 600 rpm. On the top of the reaction thermostatic unit 58, there are a plurality of recesses 60 in which the container portions of the reaction plate settle. The reaction thermostatic unit 58 consists of first place 58a and second place 58b, and two reaction plates are put in these places, so that they can be kept thermostatically (in constant temperature), shaken and agitated simultaneously. Numerals 62, 64 are holding members for grasping and holding the reaction plate from both sides.

The automated innmunochemical analyzer of the present invention is provided with only one means for aspirating and discharging the liquid sample. The means 66 for aspirating and discharging the sample liquid moves vertically for aspirating and discharging liquid. The means 66 for aspirating and discharging sample liquid is furnished with the holding part 90 for holding and lifting the reaction plate 12.

The means 66 for aspirating and discharging sample liquid having a holding part 90 is mounted on the XY moving part 70 which can move two-dimensionally on the automated immunochemical analyzer. Accordingly, the means 66 for aspirating and discharging sample liquid 66 can discharge the liquid aspirated at one position to another position, and move the reaction plate from one place to another place.

Figure 5:
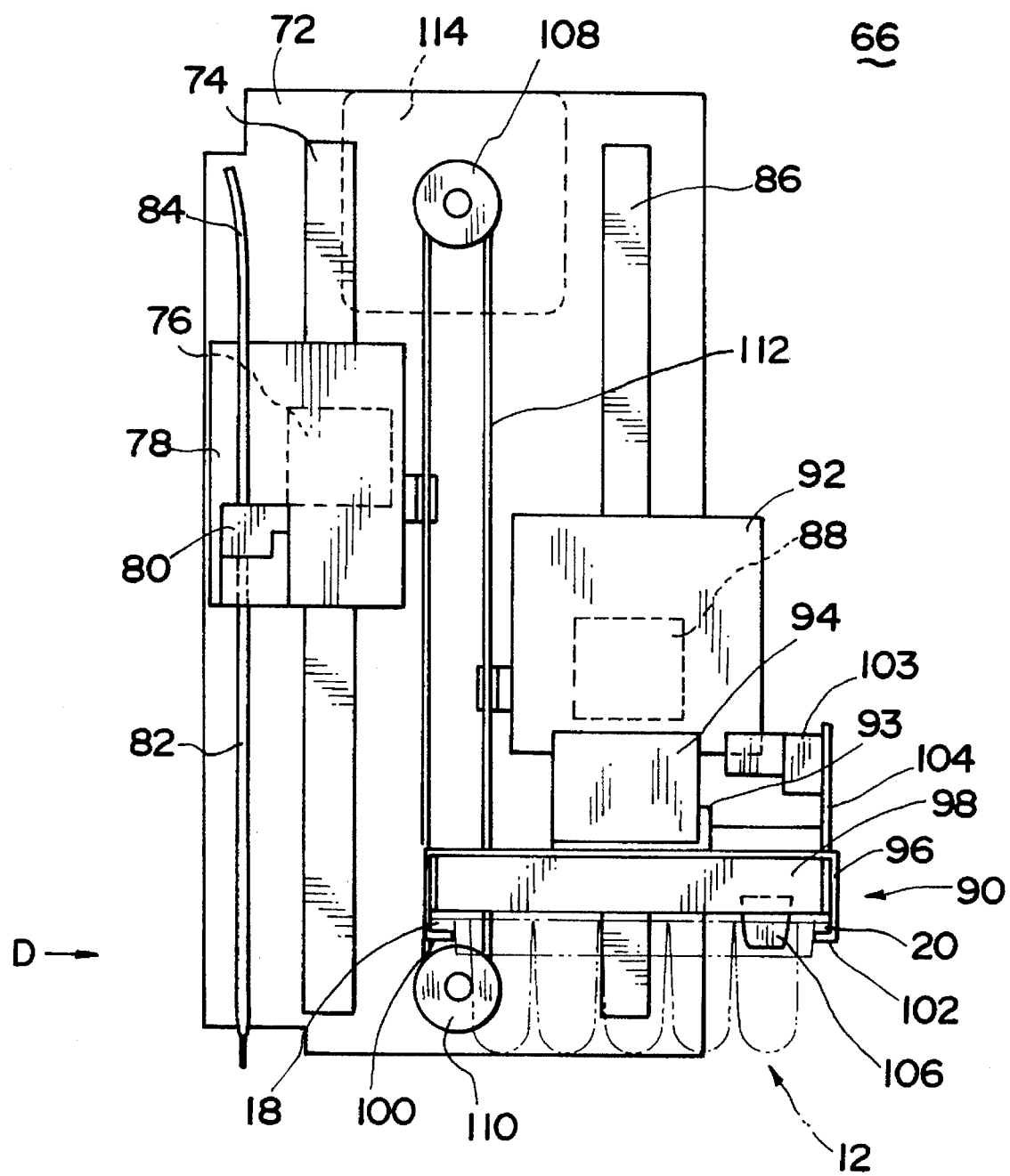
FIG. 5 is a front explanatory diagram of the means for aspirating and discharging sample liquid (as seen from the direction of arrow C in FIG. 1).

FIG. 5 is a front view of the portion of the means 66 for aspirating and discharging the sample liquid (a view in the direction of arrow C in FIG. 1). A guide rail 74 is mounted on a base plate 72. A slider 76 moves only vertically along the guide rail 74. An arm 80 is attached to the slider 76 through a mounting member 78. An aspiration piper 82 extends down from the arm 80. A tube 84 is connected to the aspiration pipet 82. Another guide rail 86 is mounted on the base plate 72 parallel to the guide plate 74, and a slider 88 moves only vertically along the guide rail 86. The slider 88 is combined with the holding part 90 for holding the reaction plate 12 through mounting members 92, 94, 93, 96. The holding part 90 comprises the mounting member 96 having the ends bent inward, that is, in a shape of notching (cutting) the middle portion of the lower side of a square, and an inside member 98 provided inside of the mounting member 96. The reaction plate 12 is held by handles 18, 20 which are fitted in bent parts 100, 102 of the holding part 90. Numeral 103 is a positioning sensor attached to a vertical member 104.

Figure 6:
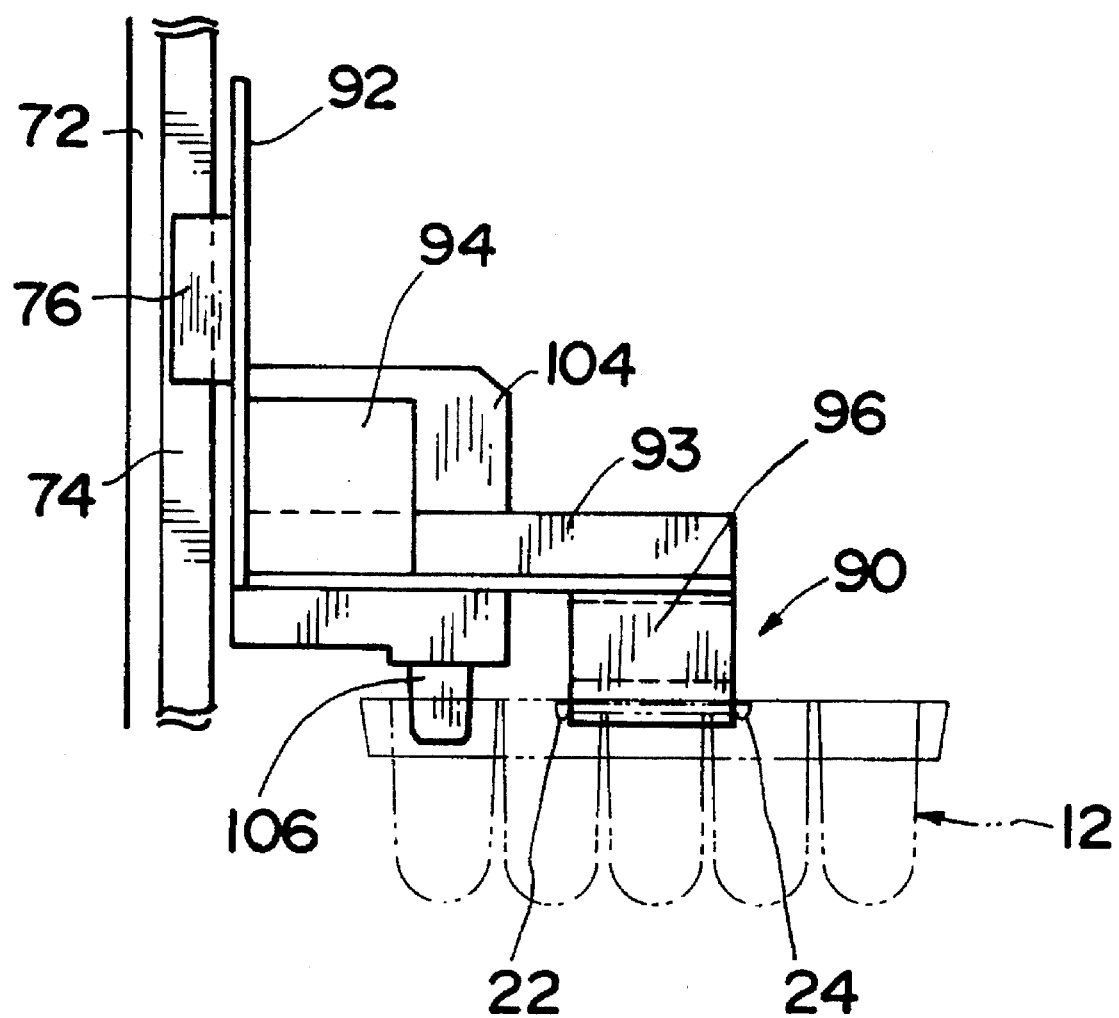
FIG. 6 is a side explanatory view of the reaction plate holding part (as seen from the direction of arrow D in FIG. 5).

FIG. 6 is a view of the holding part 90 as seen from its side (a view in the direction of arrow D in FIG. 5). Since protrusions 22, 24 for holding provided in the lower part at both ends of the handle 18 of the reaction plate 12 are located so as to grasp the bent part 100 from both sides, and the reaction plate 12 is lifted up while maintaining the specific position, there is no deviation in position. Furthermore, the base plate 72 is provided with a columnar member 106 with round ends through the vertical mender 104, and the columnar member 106 is designed to be fitted into one container of the reaction plate 12 when the reaction plate 12 is held and lifted by the holding part 90. Hence, the reaction plate 12 is fixed firmly, and is not deviated or loosened in spite of longitudinal or lateral movement.

The base plate 72 is rotatably provided with a pair of pulleys 108, 110, and a belt 112 is applied on the pulleys 108, 110. One pulley 108 is coupled with the rotary shaft of a motor 114, and the belt 112 can rotate both normally and in the reverse. The mounting member 78 is connected to one side of the belt 112, while the mounting member 92 is connected to the other side of the belt 312. Hence, the arm 80 and holding part 90 move mutually in reverse directions. That is, when the arm 80 ascends, the holding part 90 descends, and when the arm 80 descends, the holding part 90 ascends. Comparing the frequency of liquid aspirating and discharging action and the holding action of the reaction plate, the frequency of liquid aspiration and discharge is higher by far, and it is not necessary to do both actions simultaneously, there is no problem with moving the arm 80 and holding part 90 up and down alternately by one motor 114. When the holding part 90 is lowered in order to hold the reaction plate (or release the held reaction plate), the piper 82 goes up, and hence there is no obstacle to holding (or releasing) the reaction plate. When the piper 82 is lowered for aspiration or distribution of liquid, the holding part 90 goes up, and there is no problem with the aspirating and discharging action.

The actual operation is described below with reference to FIG. 1.

The means 66 for aspirating and discharging sample liquid provided with the holding part 90 of the reaction plate moves to above the first place 32a on the table 10, where the holding part 90 descends, and the reaction plate 12a is held. After holding the reaction plate, the holding part 90 ascends and moves to above the first reaction part 58a of the reaction thermostatic unit 58, and places the held reaction plate 12a onto the unit 58. The reaction plate 12b is similarly moved from the second place 32b on the table 10 to above the second reaction part 58b and onto the unit 58.

Next, by the means 66 for aspirating and discharging sample liquid, specimen, buffer solution and latex reagent are sequentially aspirated in specific volumes, and sequentially discharged into empty containers 14 of the reaction plate placed on the reaction thermostatic unit 58. For example, 100 μ of reaction liquid composed of 10 μ of specimen, 80 μ of buffer solution and 10 μ of latex reagent is held thermostatically and shaken and agitated, and the agglutination reaction of latex particles by the antigen-antibody reaction is promoted. Until the time of measurement, the reaction liquid is prepared for each specimen one after another. Numeral 116 is a cleaning tank for cleaning (rinsing) the piper 82. If necessary, the specimen is preliminarily diluted by adding a diluent liquid.

When the reaction for a specific time is over, the reaction liquid is sampled in the means 66 for aspirating and discharging sample liquid, distributed in a measuring chamber 118, and transferred to a measuring unit (not shown) and measured. A practical example of a measuring unit is disclosed, for instance, in the Published Japanese Laid open Patent Hei. 1-259257.

When all containers of the reaction plates are used up, the used reaction plates are moved to the places 32c, 32d on the table 10. Then, the table 10 is drawn out, and the used reaction plates are discarded (dumped), and new reaction plates are put in places 32a, 32b. These placing and removing actions of reaction plates can be done also while the apparatus is in action. It is the same for placing and removing of specimen racks. Near the tables 10, 34, display means showing possible/impossible to draw out is provided, for example, the green lamp means (displays) possible and the red lamp impossible, and according to the display the drawing action can be done. Even in the impossible state, by entering the draw-out reserve, it can be set in the possible state for drawing out by changing the sequence (however, the important sequence such as the reaction condition that may affect the result of measurement is not changed).

Figure 7:
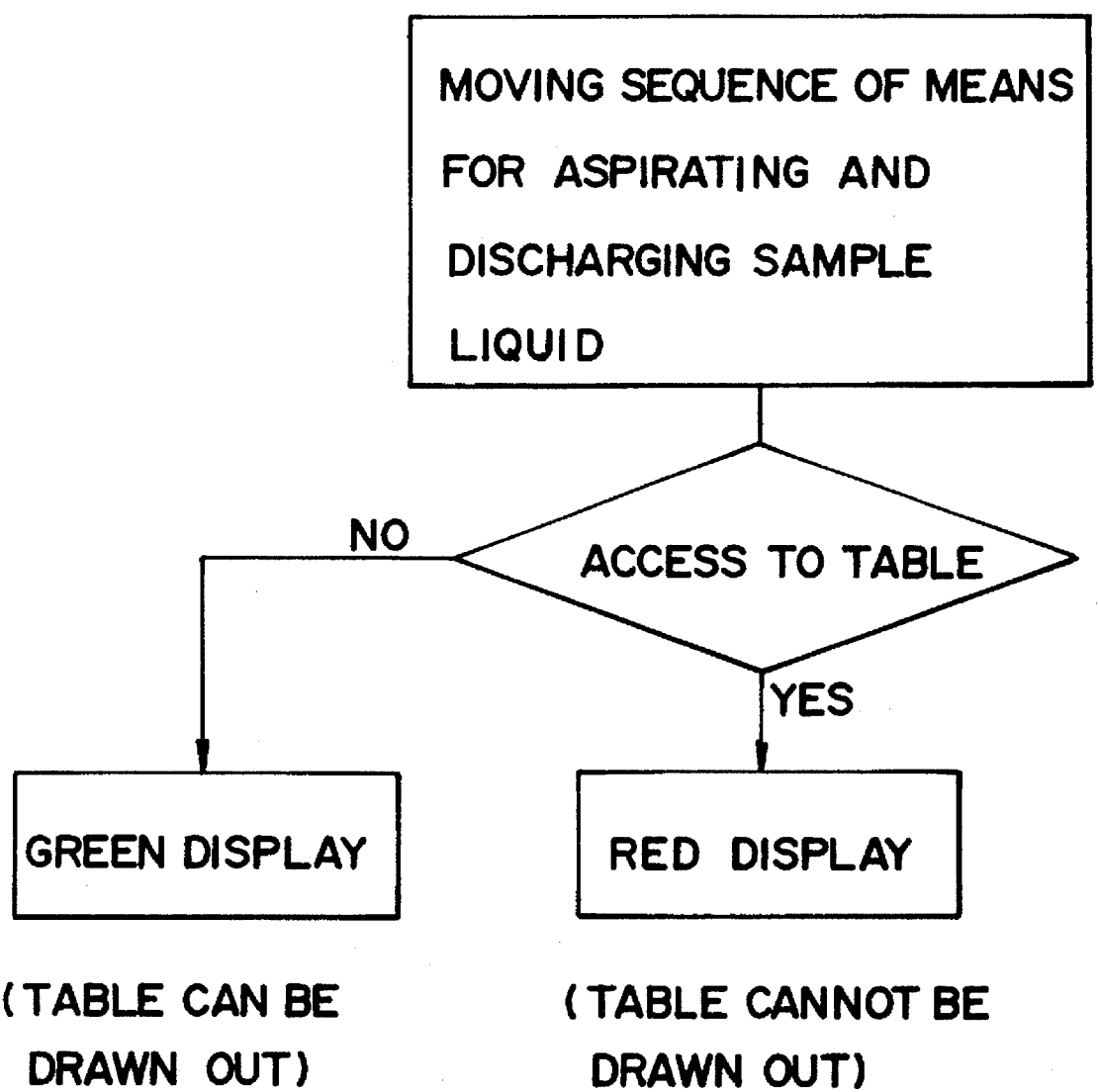
FIG. 7 is a flow chart showing a display method for the display means.

FIG. 7 is a flow chart showing the display method of the display means. To display in the table for a specimen rack, it is judged and displayed possible/impossible to draw out depending on whether the means 66 for aspirating and discharging sample liquid moves to the table 34 for specimen rack or not. It is the same in the case of table 10 for a reaction plate.

Figure 8:
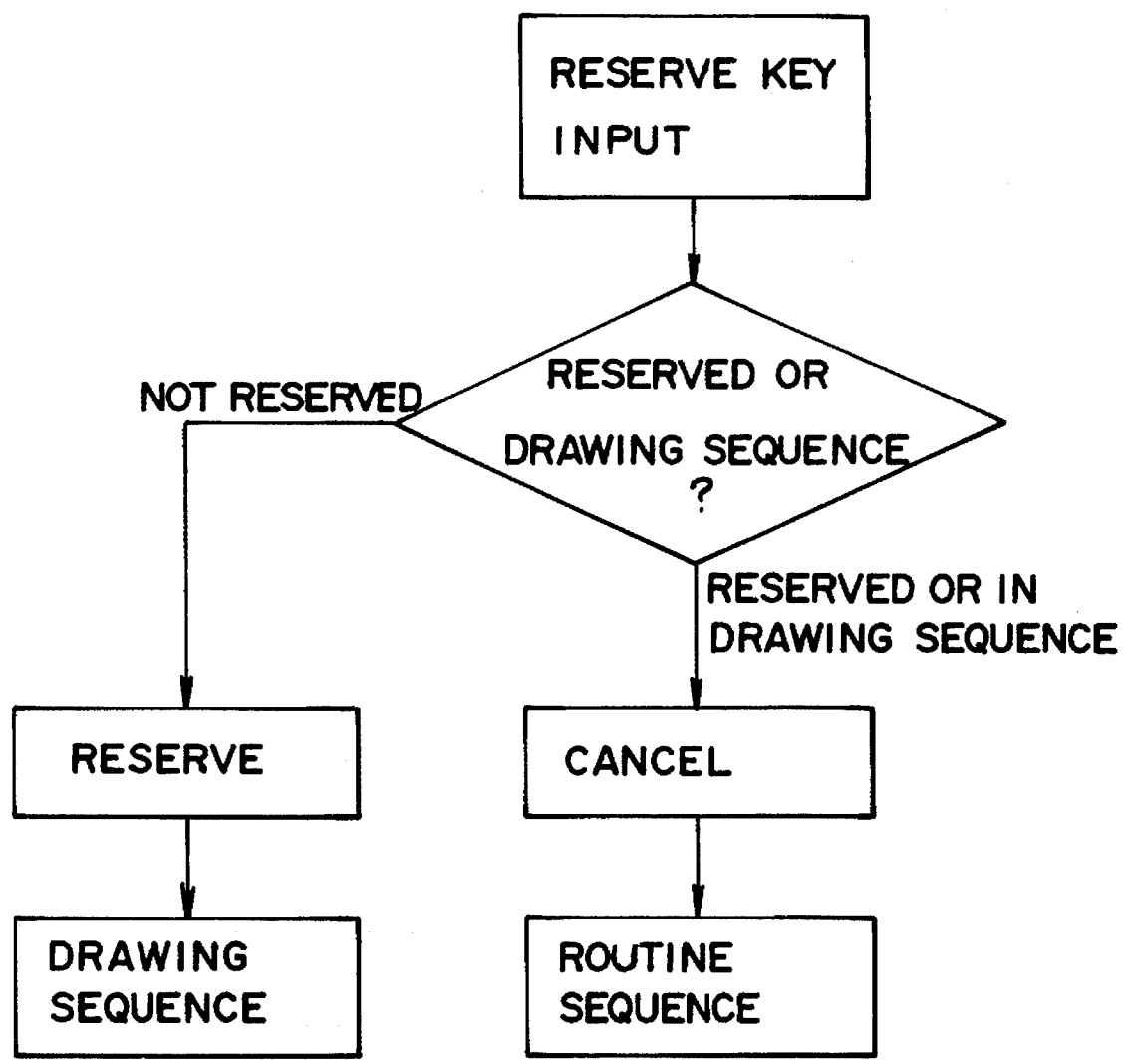
FIG. 8 is a flow chart showing reservation/cancellation of table draw-out.

FIG. 8 is a flow chart showing reserve/cancel for table drawing out. When reserved, the sequence for enabling the table to be drawing out is effected. That is, while continuing the reaction sequence or measurement sequence of specimens, the means 66 for aspirating and discharging sample liquid is prevented from accessing the table. In the draw-out sequence, as shown in FIG. 7, the display turns to green, and it is ready to draw out. After closing, when the reserve key is entered again, the operation returns to the routine sequence.

Figure 9:
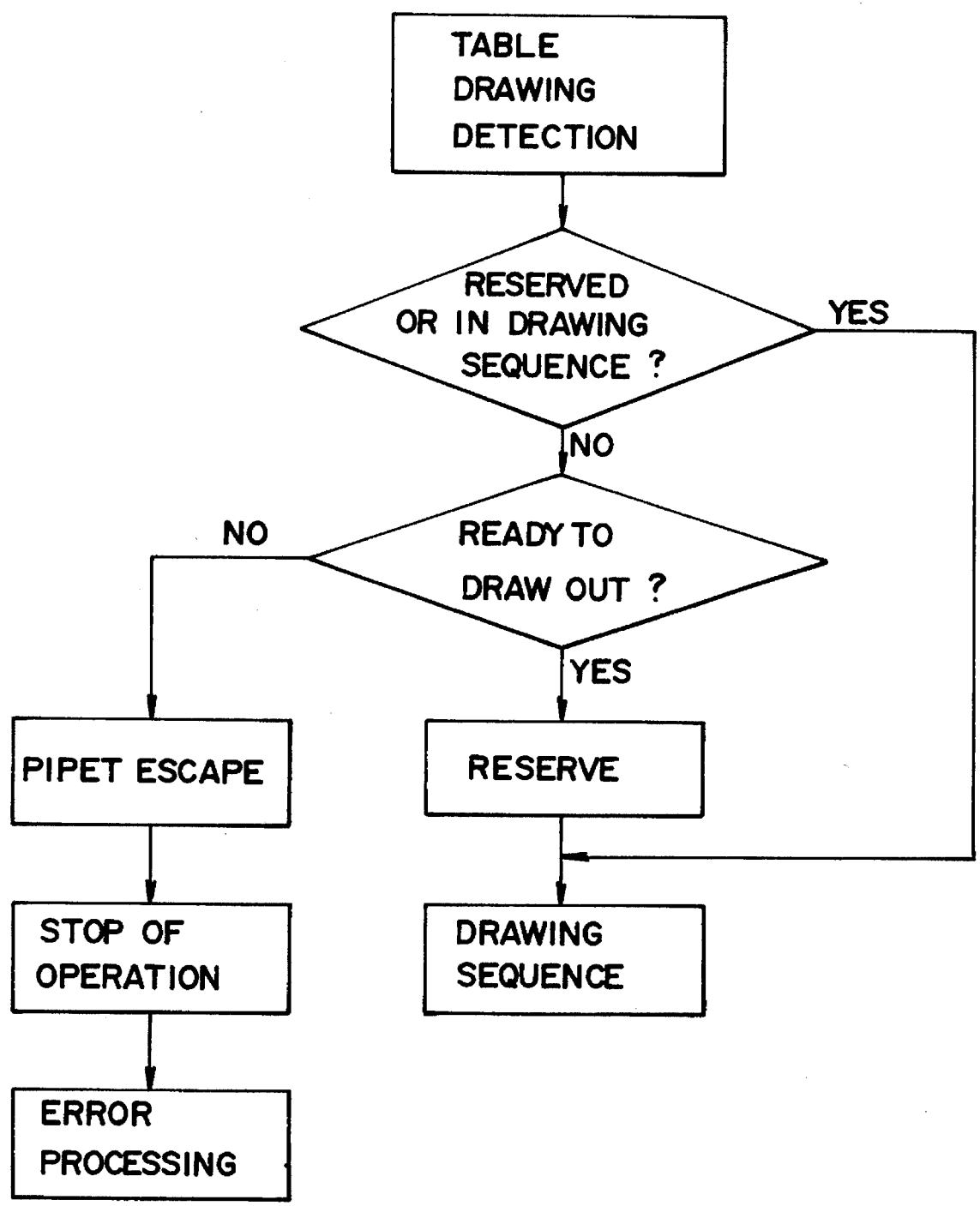
FIG. 9 is a flow chart showing the drawing processing of the table.

FIG. 9 is a flow chart showing the processing for drawing out the table. When already reserved or during a drawing sequence, the drawing sequence starts or continues. If not reserved, when set in the drawing state, it is reserved. Not in drawing state, together with an alarm, the pipet of the means 66 for aspirating and discharging sample liquid is immediately lifted to escape, and stopped, and error processing is done (conducted).

It is more preferable to provide means for locking the table drawing to actuate the locking means while the table drawing is disabled so that the table cannot be drawn out.

In the table drawing state, the locking means is invalidated, that is, the locking means does not act. Such locking means may be realized by the known art.

Being thus constructed, the present invention brings about the following effects.

(1) The reaction plate is of a disposable type, and the cleaning (rinsing) mechanism is not needed, and carry-over is eliminated, so that precision may be enhanced.

(2) Since the means for aspirating and discharging sample liquid and reaction plate holding part can be moved by the XY moving part, individual rotary mechanisms used in the conventional apparatus are not needed, and only one drive mechanism is enough, so that the structure of the apparatus may be extremely simplified.

(3) It is not necessary to dispose a plurality of specimen containers, reagent containers and reaction containers on the circumference of each turntable, and they can be laid out in rows, so that the apparatus size may be significantly reduced.

(4) By downsizing and simplifying of the apparatus, an apparatus of high reliability and low price may be provided.

(5) The specimen containers, reagent containers, and reaction containers are fixed in position, and by considering only the XY moving part which is the only one drive mechanism, addition of specimens to be measured or interruption (squeezing) with emergency specimens may be easily enabled, so that an easy-to-use apparatus is realized.

Having described preferred embodiments of the present invention with reference to the accompanying drawings, it is to be understood that the present invention is not limited to those precise embodiments, and that various changes and modifications may be effected therein by one skilled in the art without departing from the scope or the spirit of the present invention as defined in the appended claims.

What is claimed is:

1. An automated immunochemical analyzer, comprising:

at least one reaction plate;

a table for mounting said at least one reaction plate;

at least one specimen rack;

a table for mounting said at least one specimen rack, wherein the table for mounting said at least one reaction plate and the table for mounting said at least one specimen rack can be individually drawn out;

means for holding said at least one reaction plate;

means for aspirating and discharging sample liquid, having an elevatable pipet for aspirating and discharging sample liquid;

means for moving the means for holding said at least one reaction plate and the means for aspirating and discharging sample liquid simultaneously;

means for judging whether it is possible or impossible to draw out the table for mounting said at least one reaction plate, on the basis of an access status of the means for holding said at least one reaction plate to the table for mounting said at least one reaction plate;

means for displaying whether it is possible or impossible to draw out the table for mounting said at least one reaction plate on the basis of the judgment thereof;

means for judging whether it is possible or impossible to draw out the table for mounting said at least one specimen rack, on the basis of an access status of the means for aspirating and discharging sample liquid to the table for mounting said at least one specimen rack;

means for displaying whether it is possible or impossible to draw out the table for mounting said at least one specimen rack on the basis of the judgment thereof; and means for reservation, for changing a sequence from not allowing a drawing out state to allowing a drawing out state for preventing one of said means for holding said at least one reaction plate and said means for aspirating and discharging sample liquid from access to said table for mounting said at least one reaction plate and said table for mounting said at least one specimen rack, respectively, so that said tables can be drawn out, wherein a reservation is automatically set to maintain a state allowing drawing out when said tables are drawn out even if a reservation is not set.

2. An automated immunochemical analyzer as defined in claim 1, wherein:

the possibility display and the impossibility display are shown in different colors.

3. An automated immunochemical analyzer as defined in claim 1, further comprising:

means for ringing an alarm when the table for mounting said at least one reaction plate or the table for mounting said at least one specimen rack is drawn out in the period when it is impossible for drawing out the table for mounting said at least one reaction plate or the table for mounting said at least one specimen rack.

4. An automated immunochemical analyzer as defined in claim 1, further comprising:

means for locking the table for mounting said at least one reaction plate or the table for mounting said at least one specimen rack in the period when it is impossible for drawing out the table for mounting said at least one reaction plate or the table for mounting said at least one specimen rack, and unlocking the table for mounting said at least one reaction plate or the table for mounting said at least one specimen rack in the period when it is possible for drawing out the table for mounting said at least one reaction plate or the table for mounting said at least one specimen rack.

5. An automated immunochemical analyzer as defined in claim 1, wherein:

the table for mounting said at least one reaction plate includes a place for disposing reaction plates before use, and a place for disposing reaction plates after use.

6. An automated immunochemical analyzer as defined in claim 1, wherein said table for mounting said at least one reaction plate and said table for mounting said at least one specimen rack are drawn out when access thereto is prevented by said means for reservation.

* * * * *